(12) United States Patent
Gordon et al.

(10) Patent No.: US 9,993,272 B2
(45) Date of Patent: Jun. 12, 2018

(54) PEDIATRIC INTRAMEDULLARY NAIL

(71) Applicant: Orthopediatrics Corp., Warsaw, IN (US)

(72) Inventors: J. Eric Gordon, St. Louis, MO (US); Mark D. Landes, Salem, NH (US); David W. Daniels, Winona Lake, IN (US); Scott C. Brown, Warsaw, IN (US)

(73) Assignee: Orthopediatrics Corporation, Warsaw, IN (US)

( * ) Notice: Subject to any disclaimer, the term of this patent is extended or adjusted under 35 U.S.C. 154(b) by 653 days.

(21) Appl. No.: 14/033,978

(22) Filed: Sep. 23, 2013

(65) Prior Publication Data

US 2014/0018805 A1   Jan. 16, 2014

Related U.S. Application Data

(63) Continuation of application No. 12/777,369, filed on May 11, 2010, now Pat. No. 8,540,714.

(51) Int. Cl.
*A61B 17/58* (2006.01)
*A61B 17/72* (2006.01)
*A61B 17/17* (2006.01)

(52) U.S. Cl.
CPC .......... *A61B 17/72* (2013.01); *A61B 17/1725* (2013.01); *A61B 17/7233* (2013.01)

(58) Field of Classification Search
CPC . A61B 17/72; A61B 17/7208; A61B 17/7216; A61B 17/7225; A61B 17/7233; A61B 17/7241; A61B 17/725; A61B 17/7283; A61B 17/7291; A61B 17/744; A61B 17/748; A61B 17/842;
(Continued)

(56) References Cited

U.S. PATENT DOCUMENTS

| | | |
|---|---|---|
| 4,135,507 A | 1/1979 | Harris |
| 4,169,470 A | 10/1979 | Ender et al. |
| 4,622,959 A * | 11/1986 | Marcus .............. A61B 17/1721 606/64 |

(Continued)

FOREIGN PATENT DOCUMENTS

| | | |
|---|---|---|
| DE | 1593440 | 7/1981 |
| DE | 2209947 | 6/1989 |

(Continued)

OTHER PUBLICATIONS

PCT Search Report of PCT/US2011/035134 dated Sep. 12, 2011, 7pgs.

(Continued)

*Primary Examiner* — Lynnsy Summitt
(74) *Attorney, Agent, or Firm* — Woodard, Emhardt, Moriarty, McNett & Henry LLP

(57) ABSTRACT

Among other things, there are disclosed embodiments of an intramedullary nail system for use in pediatric cases, including an intramedullary nail and a targeting assembly. Embodiments of the nail may be one-piece and include a proximal portion, a medial portion and a distal portion. The junction of the medial portion and distal portion is a bend that provides a small angle between the medial portion and the distal portion as viewed when the nail is substantially in a medial-lateral plane. The targeting assembly attaches to the proximal portion of the nail securely and enables easy insertion of fixing screws.

20 Claims, 6 Drawing Sheets

(58) Field of Classification Search
CPC . A61B 17/846; A61B 17/848; A61B 17/1725; A61B 17/921; A61B 17/1717
See application file for complete search history.

(56) References Cited

U.S. PATENT DOCUMENTS

| | | | |
|---|---|---|---|
| 4,911,153 A | | 3/1990 | Border |
| 5,041,115 A * | | 8/1991 | Frigg ............... A61B 17/72 606/62 |
| 5,201,735 A * | | 4/1993 | Chapman ........... A61B 17/72 606/62 |
| 5,478,341 A | | 12/1995 | Cook |
| 5,549,601 A | | 8/1996 | McIntyre et al. |
| 5,549,610 A * | | 8/1996 | Russell ............ A61B 17/7241 606/62 |
| 5,766,174 A * | | 6/1998 | Perry ............. A61B 17/1725 606/62 |
| 5,766,179 A | | 6/1998 | Faccioli et al. |
| 6,080,159 A * | | 6/2000 | Vichard ........... A61B 17/1725 606/64 |
| 6,221,074 B1 * | | 4/2001 | Cole ................ A61B 17/72 606/60 |
| 6,629,976 B1 * | | 10/2003 | Gnos ............... A61B 17/7291 606/62 |
| 7,008,425 B2 * | | 3/2006 | Phillips ............ A61B 17/7208 606/62 |
| 7,771,428 B2 * | | 8/2010 | Siravo .............. A61B 17/72 606/62 |
| 7,842,036 B2 * | | 11/2010 | Phillips ............ A61B 17/7208 606/62 |
| 2003/0069581 A1 * | | 4/2003 | Stinson ............. A61B 17/921 606/62 |
| 2005/0277936 A1 | | 12/2005 | Siravo |
| 2007/0123873 A1 * | | 5/2007 | Czartoski ............ A61B 17/72 606/62 |
| 2007/0288017 A1 * | | 12/2007 | Kaup ................. A61B 17/72 606/62 |
| 2008/0183171 A1 * | | 7/2008 | Elghazaly ........... A61B 17/744 606/64 |
| 2009/0326541 A1 | | 12/2009 | Metzinger |

FOREIGN PATENT DOCUMENTS

| | | |
|---|---|---|
| EP | 0 321 170 | 6/1989 |
| EP | 0 381 462 | 8/1990 |
| EP | 0 521 600 | 1/1993 |
| EP | 0 684 794 | 12/1995 |
| EP | 0 706 782 | 4/1996 |
| EP | 0 715 832 | 6/1996 |
| EP | 0 777 446 | 6/1997 |
| EP | 0 827 717 | 3/1998 |
| EP | 0 838 199 | 4/1998 |
| EP | 1 018 318 | 7/2000 |
| EP | 1 024 762 | 8/2000 |
| EP | 1 113 759 | 7/2001 |
| EP | 1 196 101 A1 | 4/2002 |
| EP | 1 260 188 | 11/2002 |
| EP | 1 330 988 | 7/2003 |
| EP | 1 545 356 | 6/2005 |
| EP | 1 639 953 | 3/2006 |
| EP | 1 694 230 | 8/2006 |
| EP | 1 718 223 | 11/2006 |
| EP | 1 830 727 | 9/2007 |
| EP | 1 839 608 | 10/2007 |
| EP | 1 839 612 | 10/2007 |
| EP | 1 859 750 | 11/2007 |
| EP | 2 133 034 | 12/2009 |
| EP | 2 166 973 | 3/2010 |
| EP | 2 292 166 | 3/2011 |
| WO | WO 2010/014694 | 2/2010 |
| WO | WO 2010/037038 | 4/2010 |
| WO | WO 2010/091242 | 8/2010 |
| WO | WO 2010/140991 | 12/2010 |
| WO | WO 2011/028520 | 3/2011 |

OTHER PUBLICATIONS

PCT Written Opinion for PCT/US2011/035134 dated Sep. 12, 2011 8pgs.

* cited by examiner

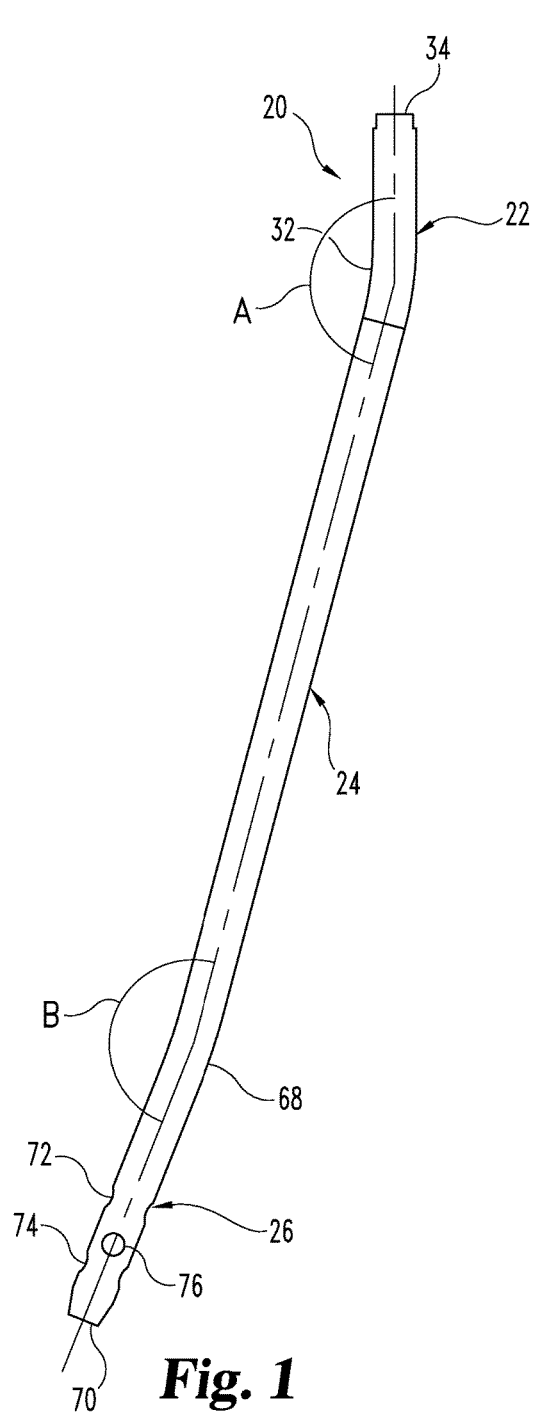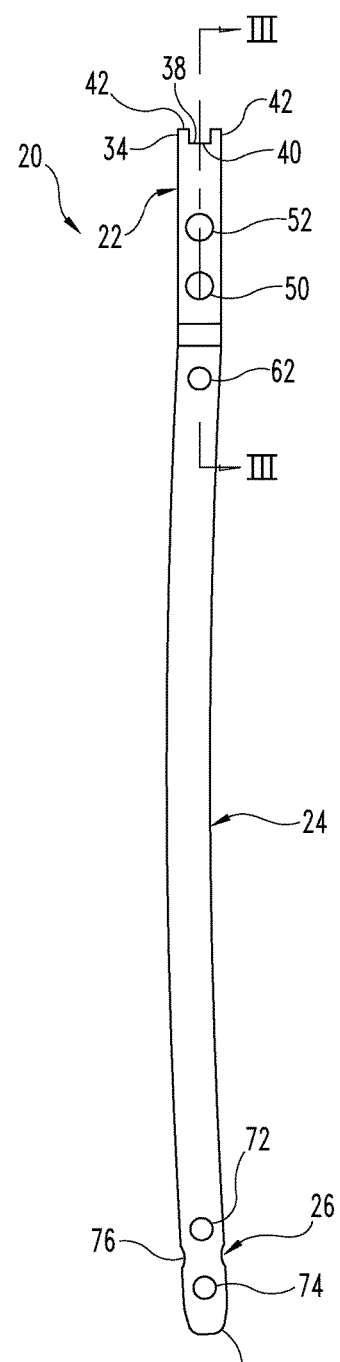
Fig. 1
Fig. 2

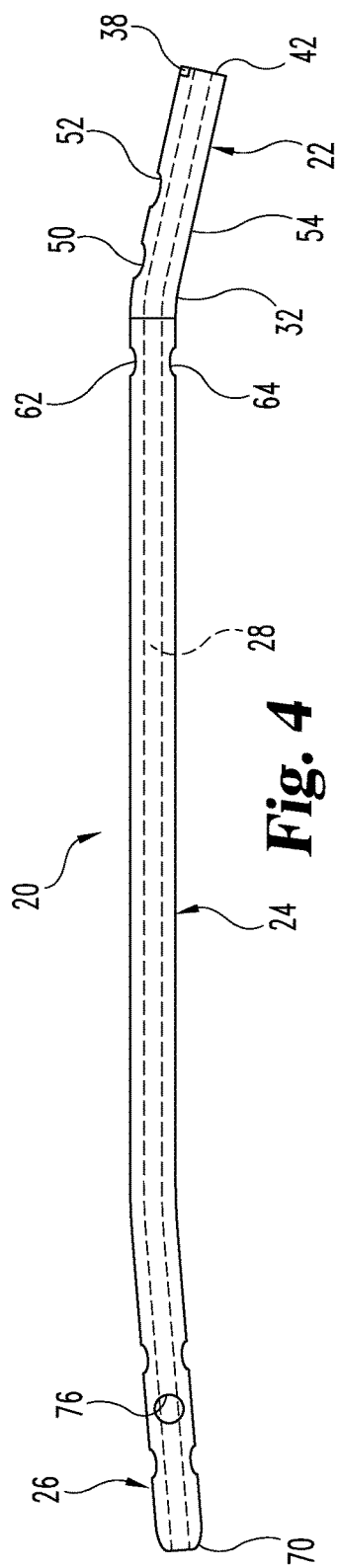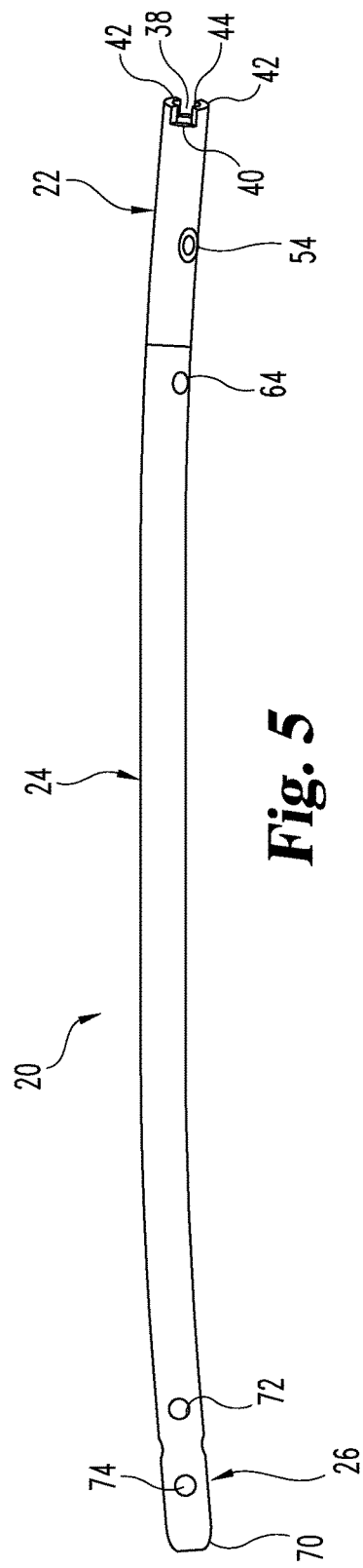

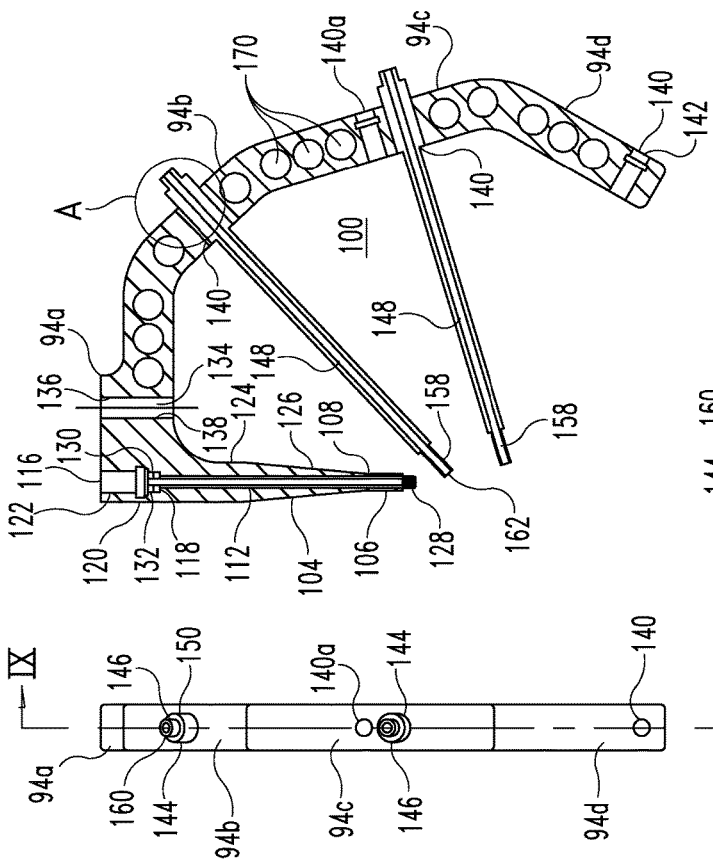
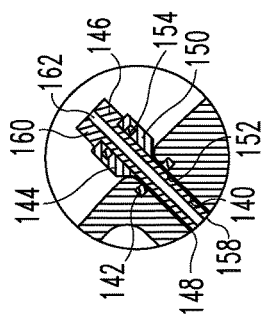
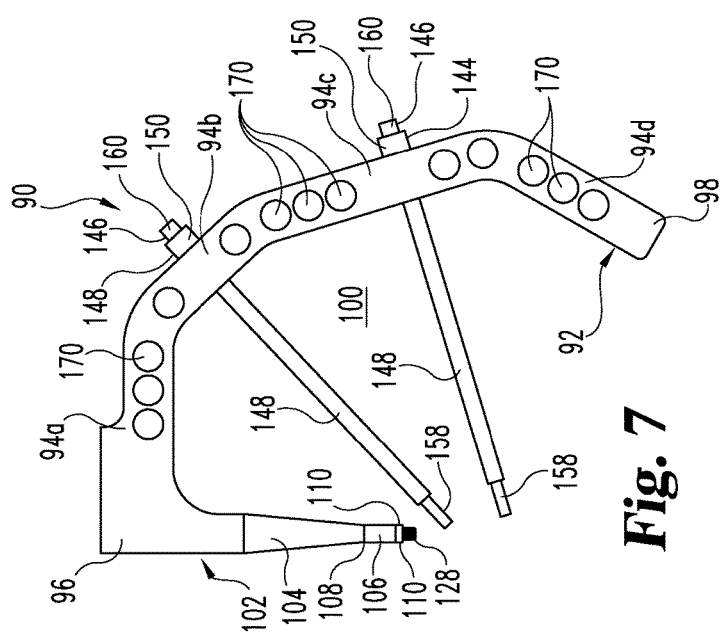

PEDIATRIC INTRAMEDULLARY NAIL

The present disclosure concerns an intramedullary nail for use in pediatric long bones, particularly the femur. In particular, the following disclosure discusses structures and methods for use in repairing such bones in the context of special issues facing pediatric patients.

BACKGROUND

In the field of orthopedic surgery, a number of devices, systems and methods known for correcting bone breaks of varying severity. For breaks of relatively low severity in the long bones (e.g. femur, tibia, fibula, radius, ulna, humerus), manual setting or perhaps an inserted screw with an external cast may be used. As the severity increases, it is known to place a series of internal or external screws to hold bone pieces in place while healing occurs. For some injuries to the long bones, or for correction of problems due to disease or other agents, it is known to open a passage to the medullary canal, remove material from the canal, and place an elongated support within the canal. The elongate support is commonly referred to as an intramedullary nail.

Existing intramedullary nails were developed and are manufactured for use in adult patients. If a surgeon believes that use of an intramedullary nail is indicated in treating a child, he or she is faced with the decision either to use a nail intended for a very small adult, or to cut down an available device as best he or she can to fit the particular case. In some cases, of course, the lack of an intramedullary nail intended for a child will make that treatment option unavailable.

The inventor of the present disclosure has realized that when it comes to orthopedic treatment and particularly surgery, children are not merely small adults. Because of their particular physiological attributes, especially ongoing physical growth, a child's bones have different characteristics and a child's body generally reacts to trauma, deformity and other problems in a somewhat different fashion compared to the body of an adult. These special characteristics of a child mean that implants and methods of implantation intended for adults, the development and creation of which occurred without consideration for the growth physiology and other special attributes of a child, frequently are not only unsuited to pediatric use, but in some cases introduce other difficulties to healing or the overall development of the child.

Intramedullary nails inserted into the femur, as an example, are generally inserted through the greater trochanter of the femur in adult patients. However, in a child's growing femur, the greater trochanter is the location of important blood vessels, and the angle between the head of the femur and the diaphysis is slightly larger than in adult femurs. Damage to those blood vessels may result in avascular necrosis of bone tissue and slowed or limited growth of the bone. There remains a need for an intramedullary nail that is specially adapted to be used in pediatric situations, which adequately provides support and assistance in healing a long bone but also avoids problems unique to children.

SUMMARY

Among other things, there are disclosed embodiments of an intramedullary nail and devices and methods for implantation, which are particularly useful in pediatric cases. These embodiments include an intramedullary nail system having an intramedullary nail that is a one-piece item with a proximal portion, a medial portion and a distal portion and a continuous cannula that extends through each of those portions. The proximal portion has a longitudinal axis and an end with at least one finger extending parallel to that longitudinal axis from an end surface. The proximal portion also has an internal thread along the cannula extending from the end surface toward the medial portion and first and second linear channels formed through the proximal portion. The first and second channels have respective first and second openings on one side of the proximal portion and a common third opening across from the first and second openings. The medial portion joins the proximal portion at a bend as viewed in a medial-lateral plane that forms an angle between the portions of about 165 degrees, and has a linear channel therethrough that is non-parallel to either of the channels in the proximal portion. The distal portion joins the medial portion at a bend as viewed in a medial-lateral plane that forms an angle between them of about 175 degrees. The distal portion has two linear channels that are parallel to each other and another linear channel between and non-parallel with the parallel channels. In some embodiments, the at least one finger of the nail has an exterior that is part-cylindrical and has a curvature matching that of the proximal portion of said nail.

The system can also include a targeting assembly adapted to be connected to the proximal portion of the nail. Embodiments of the assembly can include a bracket having first and second ends and multiple linear segments joined together between the ends, with an extension extending perpendicular to one of the segments at the first end that has a tip distal from that segment. The tip has at least one finger extending longitudinally and configured to fit alongside the at least one finger of the nail. The extension has a linear lumen through its entirety, the lumen having an at least partially internally threaded upper portion and a lower portion smaller in diameter than the upper portion. The assembly can further include a bolt having a threaded shaft and a head inserted into the lumen, the head having a diameter less than that of the upper portion of the lumen but greater than that of the lower portion of the lumen. The threaded shaft is threadedly compatible with the internal thread of the nail. The extension may have a proximal part joining a segment, a medial part in the shape of a circular cone that tapers from a first diameter adjoining the proximal part to a second diameter, and a distal cylindrical portion having a diameter smaller than that second diameter. The at least one finger of the extension may extend parallel to the axis of the distal cylindrical part and have an external surface that is part-cylindrical and continuous with the distal cylindrical part.

The nail may have a variety of configurations in different embodiments. For example, the channel in the medial portion may intersect the cannula substantially perpendicularly to the longitudinal axis of the cannula, and the parallel channels in the distal portion may intersect the cannula substantially perpendicularly to the longitudinal axis of the cannula. Another channel in the distal portion can intersect the cannula substantially perpendicularly to the longitudinal axis of the cannula, and not intersect and be substantially perpendicular to the parallel channels in the distal portion.

In other embodiments, an apparatus is disclosed including a one piece intramedullary nail having a proximal portion, a medial portion and a distal portion. The proximal portion has a longitudinal axis and an end with at least one finger extending parallel to that longitudinal axis from an end surface, and an internal thread extending from the end surface toward the medial portion. The proximal portion has first and second linear channels formed through it, those channels having respective first and second openings on one side of the proximal portion and a common third opening across from the first and second openings. The medial portion joins the proximal portion at a bend in a medial-lateral plane between the proximal and medial portions, and it has a third linear channel therethrough that is non-parallel to either of the two channels in the proximal portion. The distal portion joins the medial portion at a bend in a medial-lateral plane that forms an angle between the medial and distal portions of about 175 degrees, and the distal portion has at least one linear channel therethrough.

In particular embodiments, a targeting assembly including an extension with at least one finger at a tip may be included, with the at least one finger adapted to interengage with the at least one finger of the nail. The extension may have a longitudinal axis, and when the at least one finger of the extension is interengaged with the at least one finger of the nail, the extension cannot rotate around its axis with respect to the nail. The extension also may include a lumen therethrough, and a bolt extending through the lumen that has a threaded tip adapted to thread into the internal thread of the proximal portion of the nail. In other embodiments, the assembly includes a plurality of straight segments in non-linear engagement, each of the segments having a respective lumen. When the extension is connected to the nail, each such lumen is substantially in line with one of the linear channels in the proximal or medial portions of the nail. The assembly may include at least one respective tube extending through each lumen.

In some embodiments of the nail, the at least one finger includes a pair of fingers, each having a cylindrical exterior matching the exterior of the proximal portion, and the fingers define a slot between them. The slot may include a floor adjacent said internal thread. In other embodiments, the medial portion has a longitudinal axis and the distal portion has a longitudinal axis, and the axis of the distal portion is bent between about 1 and 10 degrees from the axis of the medial portion when viewed in a medial-lateral plane. In particular, the axis of the distal portion may be bent about 5 degrees from the axis of the medial portion when viewed in a medial-lateral plane. One channel of the nail's proximal portion may have an angle of about 45 degrees with respect to a longitudinal axis of the proximal portion, and the other may have an angle of about 120 degrees with respect to a longitudinal axis of said proximal portion. These angles have been found to be particularly useful for pediatric cases.

Methods are also disclosed. Among them is a method of implanting an intramedullary nail in the femur, including providing an intramedullary nail having a central portion and a distal portion, with the distal portion and central portion having a bend between them including an angle of between 170 and 179 degrees as viewed in a medial-lateral plane. Methods may also include making a lateral opening in the femur inferior to the physis of the greater trochanter, and inserting the intramedullary nail into the medullary canal of the femur through that lateral opening. These and other embodiments of apparatus and methods will be evident from the present description.

BRIEF DESCRIPTION OF THE DRAWINGS

FIG. 1 is a side view of an embodiment of an intramedullary nail for the right femur according to the present disclosure, viewed from the anterior (the plane of the page being a medial-lateral plane) when implanted in a right femur.

FIG. 2 is a is a view of the embodiment of FIG. 1 rotated 90 degrees to the left as seen in FIG. 1, indicating a view substantially from medial outward when implanted.

FIG. 4 is a side view of the embodiment as in FIG. 1 viewed from the posterior when implanted in a right femur.

FIG. 5 is a perspective view of the embodiment of FIG. 4.

FIG. 7 is a side view of an apparatus for use in implanting embodiments of intramedullary nails shown in FIGS. 1 and 4.

FIG. 8 is a side view of the apparatus of FIG. 7 rotated 90 degrees to the left as seen in FIG. 7.

FIG. 9 is a cross-sectional view of the apparatus of FIG. 7, taken along the lines VIII-VIII in FIG. 8 and viewed in the direction of the arrows.

FIG. 10 is a close-up view of the portion A indicated in FIG. 9.

DETAILED DESCRIPTION OF THE ILLUSTRATED EMBODIMENTS

Figure 3:
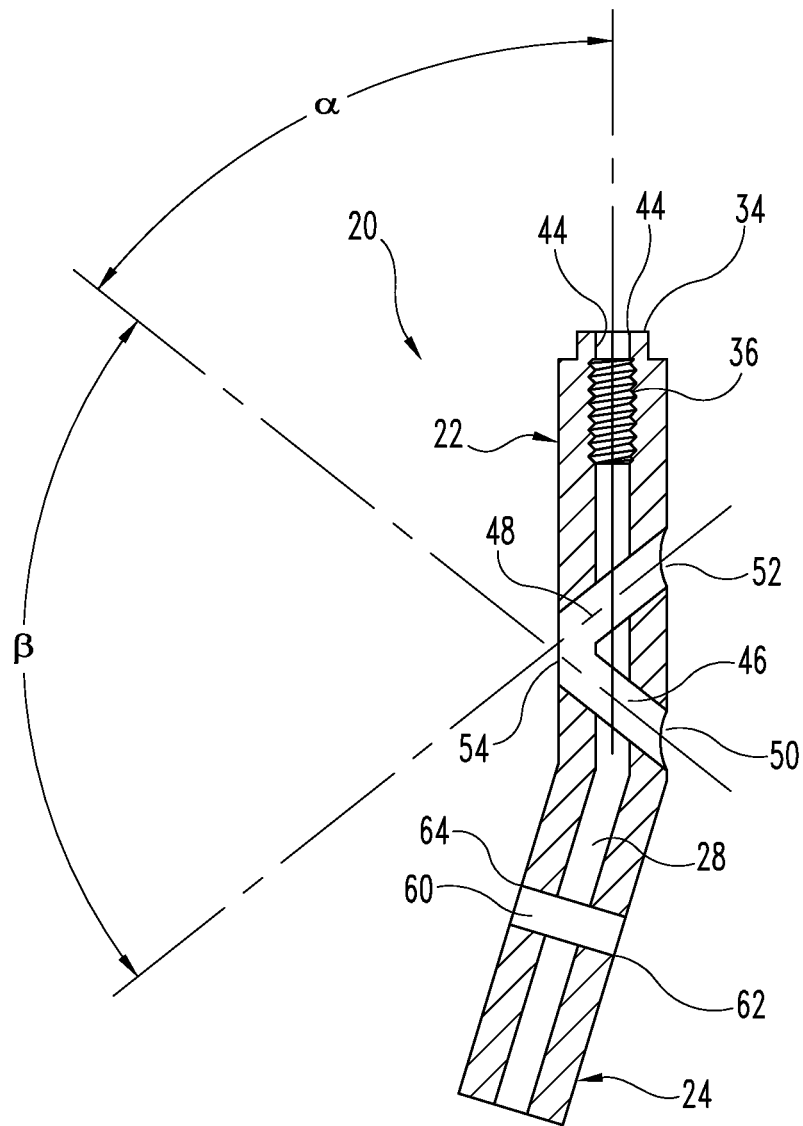
FIG. 3 is a partial cross-section of the embodiment of FIG. 2, taken along the lines III-III of FIG. 2 and viewed in the direction of the arrows.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, and alterations and modifications in the illustrated devices and methods, and further applications of the principles of the disclosure as illustrated therein are herein contemplated as would normally occur to one skilled in the art to which the disclosure relates.

Referring initially to FIGS. 1-5, there are shown embodiments of a pediatric intramedullary nail 20. Nail 20 is a one-piece elongated member in that embodiment that includes a proximal section 22, a central section 24, a distal section 26, and a cannula 28 extending through each of sections 22, 24 and 26. As will be discussed further below, each section has a particular bend where it adjoins another section.

Proximal portion 22 of nail 20 is the portion that will enter the bone last and therefore will be closest (most proximal) to the surgeon during implantation. Proximal portion 22 adjoins central portion 24 at a bend 32 of approximately 15 degrees from linear, i.e. so that portions 22 and 24 make an internal angle measuring about 165 degrees in a medial-lateral plane (e.g. viewed from an anterior position as in FIG. 1) in a particular embodiment. Proximal portion 22 terminates opposite bend 32 in an end 34. Cannula 28 extends through end 34, with a portion of cannula 28 at or adjacent end 34 having an internal thread 36. End 34 also has a slot 38 defined by a floor surface 40 and two upright fingers 42. In the illustrated embodiment, surface 40 is substantially perpendicular to the longitudinal axis of cannula 28 at end 34, and fingers 42 are substantially parallel with that axis and have part-cylindrical surfaces 44 facing each other.

Proximal portion 22 is straight in a medial-lateral plane between end 34 and bend 32 in the illustrated embodiment, as seen in FIGS. 1 and 2. Internal thread 36 has an external (root) diameter and an internal (crest) diameter, with the internal diameter being greater than the diameter of cannula 28. As cannula 28 approaches internal thread 36, the diameter widens to accommodate the internal thread 36.

Between end 34 and bend 32 are a pair of holes or channels 46, 48. Channels 46 and 48 have separate openings 50 and 52 on one side of nail 20, and share an opening 54 of the other side of nail 20. In the illustrated embodiment, openings 50, 52 are on the side of nail 20 facing away from the interior of the angle formed by bend 32, and opening 54 is within that angle. Channel 46 has a generally cylindrical cross-section (i.e., measured perpendicular to the longitudinal axis of channel 46) throughout, and it is oblique to the longitudinal axis of cannula 28 at their intersection. Due to that obliqueness of channel 46, opening 50 in the side of nail 20 will not be circular, but will be an oval. In a particular embodiment, the angle $\alpha$ measured from the longitudinal axis of cannula 28 at end 34 to the axis of channel 46 toward the interior of the angle formed by bend 32 is about 45 degrees. In the case of the femur, that angle has been determined to be efficacious for recon screws through nail 20 and toward or into the femoral head, because of the somewhat greater angle between the femoral head and the shaft in children as compared to adults. Likewise, channel 48 has a generally cylindrical cross-section (i.e., measured perpendicular to the longitudinal axis of channel 48) throughout, and it is oblique to the longitudinal axis of cannula 28 at their intersection. Due to that obliqueness of channel 48, opening 52 in the side of nail 20 will not be circular, but will be an oval. In a particular embodiment the angle $\beta$ measured from the longitudinal axis of cannula 28 at end 34 to the axis of channel 48 toward the interior of the angle formed by bend 32 is about 120 degrees. That angle has been determined to present an efficacious angle for forward screws through nail 20 into the shaft of the long bone in light of the special needs of children.

Channels 46 and 48 join at or near opening 54. Due to the obliqueness of channels 46 and 48 and to the joinder of channels 46 and 48 at or near opening 54, it will be seen that opening 54 is elongated, and in the illustrated embodiment the elongation of opening 54 is substantially greater than the elongation of either of openings 50 and 52. The elongation of opening 54 makes it possible to insert a screw or other fixation member through either channel 46 or channel 48. If the fixation member is inserted through channel 46, then it extends through openings 50 and 54 to point generally (in the case of use in a femur) in the direction of the head, while if the fixation member is inserted through channel 48, it extends through openings 52 and 54 to point generally in a medial-inferior direction.

Proximal portion 22 adjoins central portion 24 at bend 32, and in the illustrated embodiment bend 32 provides an angle between proximal portion 22 and central portion 24 in the medial-lateral plane when implanted, giving a change of direction between portions 22 and 24 as seen in FIGS. 1, 2 and 3. A view from medial outward (FIG. 2) shows proximal portion 22 with a smooth curve with central portion 24 in that particular plane. Taking a medial-lateral planar view of nail 20, as in FIG. 1, three specific sections 22, 24, 26 are seen, having discrete bends 32, 68 between them which form angles A and B (as seen in FIG. 1). These configurations create an "anterior bow" form for nail 20.

Central portion 24 of nail 20 includes a portion of cannula 28 along the longitudinal axis of portion 24. A channel 60 extends through central portion 24, with openings 62 and 64 in the sides of central portion 24. Channel 60 is substantially perpendicular to the longitudinal axis of central portion 24 (FIG. 3) in the illustrated embodiment. In that embodiment, openings 62 and 64 are thus substantially circular, and channel 60 forms an angle of about 70 degrees with respect to the longitudinal axis within proximal portion 22 and an angle of about 25 degrees with respect to channel 46. Channel 60 intersects cannula 28, and in a particular embodiment channel 60 is not threaded, e.g. having a smooth internal wall.

It will be noted that in the illustrated embodiment a plane can be drawn through the centers of holes 50, 52, 54, 62 and 64. Accordingly, screws that extend through those holes (as discussed further below) will also be in the same plane.

Distal portion 26 adjoins central portion 24 at a bend 68. Distal portion 26 bends inward from central portion 24 at a small angle in the medial-lateral plane (FIG. 1). In some embodiments, the angle may be up to about 10 degrees, and in the illustrated embodiment the angle is approximately 5 degrees. The included angle between portions 24 and 26 is thus about 175 degrees in the illustrated embodiment. A small angle of inward bend of portions 26 from portion 24 makes possible a lateral entrance to the medullary canal. The lateral entrance, discussed further below, allows the implantation to avoid not only growth areas of the femur, but also groups of blood vessels gathered on or around the greater trochanter. The possibility of avascular necrosis or other damage to the greater trochanter and other parts of a child's growing bone is thus minimized or eliminated through the use of a lateral entrance via a nail 20 having a distal portion having a small inward bend (or large obtuse included angle) between central and distal portions.

An end 70 that is conically tapered (as seen in one embodiment in FIGS. 1-2, 5A and others), or convexly curved (as seen in end 70' in one embodiment in FIG. 5B) also assists in placement of nail 20. End 70 has a tip of outer diameter d and a side surface 71 that widens uniformly or with a constant slope to the outer diameter D of the rest of distal portion 26. The taper of end 70 assists in inserting nail 20 through an entry into the bone. Once within the medullary canal, as noted further below, end 70 may contact the hard bone surface extending along the canal. When that happens, further insertion force on nail 20 drives the tapered portion of end 70 against the inner hard bone surface, resulting in a deflection of the tapered surface. End 70 does not press into the interior lengthwise bone surface, but instead the tapered surface slides along it, enabling more smooth turning of nail 20 into the medullary canal. The taper of surface 71 decreases the diameter in end 70 from diameter D to diameter d to a relatively small degree, for example where diameter d is about three-quarters of diameter D.

Figure 5A:
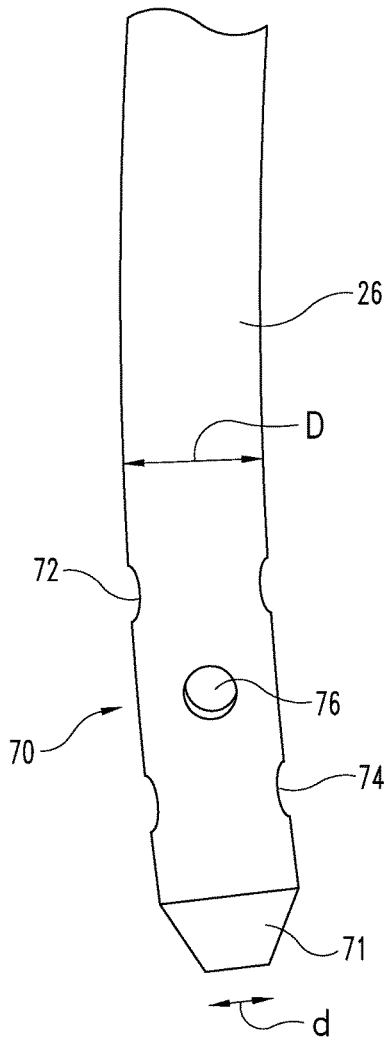
FIG. 5A is a side view of an embodiment of a distal portion of the embodiment of FIG. 1.
Figure 5B:
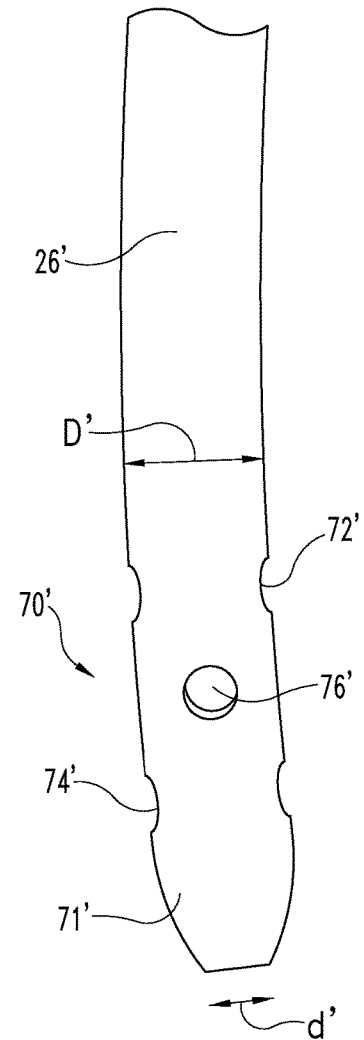
FIG. 5B is a side view of another embodiment of a distal portion associated with the rest of the embodiment of FIG. 1.

Convexly curved end 70', in the illustrated embodiment, has been found to be more effective for insertion into the particular anatomy of the intramedullary canal of a child's femur. In FIG. 5B, parts that are similar or identical to parts described with respect to FIGS. 1, 2, 5A and others are noted with corresponding primed numbers or letters. End 70' has a tip of diameter d' and a side surface 71' that widens in a curve from the tip to a diameter D' of the remainder of a distal portion 26. Looked at in longitudinal cross section or from the side (as in FIG. 5B), the curve of side surface 71' is parabolic or approximately parabolic. In other embodiments, side surface 71' in such a view may be a portion of a circumference of a circle of a radius at least as large as or larger than the outer diameter D'. The curvature of end 70' permits the tip diameter d' to be significantly smaller than that of a comparably sized nail having tapered end 70 (i.e. for nails with diameters D and D' that are the same, d' is substantially smaller than d). For example, d' may be about half of the larger diameter D' and/or just larger than the diameter of lumen 28.

End 70' also features a longer curved surface 71' compared to the tapered surface 71. In the illustrated embodiments, curved surface 71' extends from the distal end toward distal-most hole 74' so that curved surface 71' covers at least half of the distance between the distal end and hole 74'. In other particular embodiments, curved surface 71' extends further toward hole 74', such as 80 percent or more, 90 percent or more, or the entire distance between the distal end of nail 20 and hole 74'. Generally, as the overall diameter of the nail increases, the amount of the distance between the distal end and hole 74' is larger. For example, a 10 mm diameter nail has a curved surface 71' that is the entire or substantially the entire distance between the distal end and hole 74', while a 7 mm diameter nail has a curved surface 71' that is around 70 percent of the distance between the distal end and hole 74'. Such a relatively long length of curved surface 71' extends the leading portion that engages the interior of the intramedullary canal as nail 20 is inserted. That extended leading portion is believed to provide more efficient transfer of force from the canal interior to the nail in positioning the nail, and to keep the holes 72', 74', 76' (or at least the distal-most hole 74') further away from the surface of the canal (or keeps the tissue from engaging the edge of such hole(s)) during insertion, resulting in less scoring or gouging of tissue during insertion. The graduated curvature (or bullet-type shape) of surface 71' and its comparative reduction of tip diameter has been found to be easier and less traumatic to initially insert and to move through the narrow intramedullary canals of pediatric bones.

Between bend 68 and end 70 are three holes or passages 72, 74, 76 in the illustrated embodiment. Channels 72 and 74 are substantially parallel to each other and perpendicular to the longitudinal axis of distal portion 26. Hole 76 is between holes 72 and 74, and is substantially perpendicular to them. Each of holes 72, 74 and 76 communicate with cannula 28, which extends through portion 26 along the longitudinal axis of portion 26. In particular embodiments, some or all of holes 72, 74 and 76 are not threaded, e.g., they have smooth interior walls. In the illustrated embodiment the plane containing the axes of holes 72 and 74 is turned slightly with respect to the plane containing the centers of holes 50, 52, 54, 62 and 64 around the longitudinal axis of distal portion 26.

Cannula 28 extends through the entirety of nail 20, beginning at end 34 and following the longitudinal axes of each portion 22, 24, 26 to end 70. As noted previously, thread 36 at end 34 is somewhat larger in diameter than is the rest of cannula 28, and fingers 42 stand astride the exit of cannula 28 at end 34. Cannula 28 has a substantially constant diameter as it goes through portions 22, 24, and 26 in some embodiments, although in other embodiments (such as that shown in FIG. 6, discussed further below), cannula 28 may narrow and/or widen along central portion 24 and/or distal portion 26.

Figure 6:
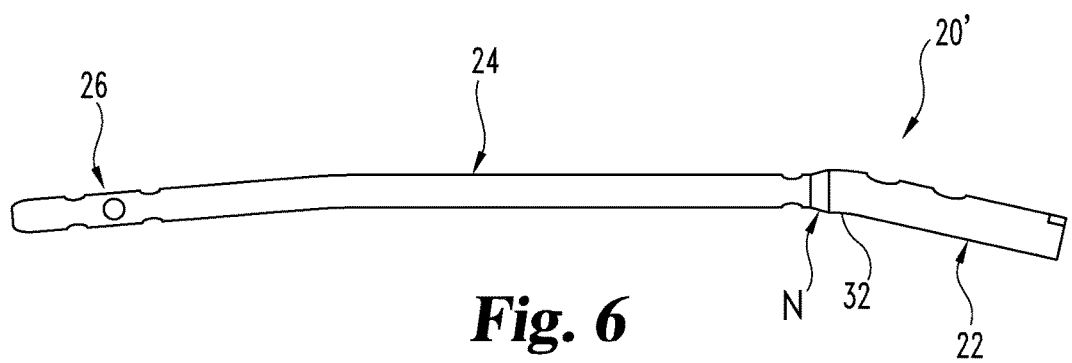
FIG. 6 is a side view of a variation of the embodiment of FIG. 1.
Figure 11:
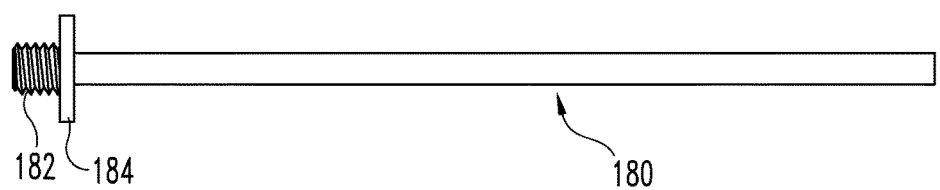
FIG. 11 is a side view of an impaction rod usable with the apparatus shown in FIG. 7.

Central portion 24 and distal portion 26 are generally of the same outer diameter, as can be seen at least in FIGS. 1-2. These portions are inserted in and through the medullary canal of the long bone, as described above, and that outer diameter is chosen for ease of insertion and sufficiency of support when placed within the bone. The embodiment of FIGS. 1-2 also show proximal portion 22 having the same outer diameter as central portion 24 and distal portion 26. Pediatric long bones can be rather narrow in the diaphysis, compared to the end parts and to adult bones. Accordingly, some embodiments of nail 20 will have a correspondingly narrow central portion 24 and distal portion 26 while having a larger proximal portion 22 to provide insertion stability. FIG. 6 shows a version of nail 20' that is similar to nail 20 in most respects. Its proximal portion 22', central portion 24' and distal portion 26' are fashioned as described above with respect to portions 22, 24 and 26, except that the outer diameter of portion 22' is larger than the outer diameters of portions 24' and 26'. As seen in FIG. 6, such an embodiment may have a narrowing portion N at the proximal end of central portion 24' or within the bend 32 between proximal portion 22' and central portion 24'. Narrowing portion N may be linearly tapered, concavely radiused, otherwise smoothly narrowed or configured to step the diameter of the proximal portion 22' down to that of the central portion 24'.

A targeting device assembly 90 for use during implantation of nail 20 is shown in one embodiment in FIGS. 7-10. Assembly 90 includes a bracket 92 that is roughly C-shaped and planar in the illustrated embodiment. That embodiment includes four straight segments 94a, 94b, 94c, and 94d connected in series. An end 96 of bracket 92 is the free end of segment 94a. Segment 94b connects to the other end of segment 94a, and is angled with respect to segment 94a with an angle of about 135 degrees included between segments 94a and 94b in the illustrated embodiment. Segment 94c connects to segment 94b, and an angle of about 150 degrees is included between segments 94c and 94b in the illustrated embodiment. Segment 94d includes end 98 of bracket 92 at its free end, and its other end is connected to segment 94c so that another angle of about 135 degrees is included between segments 94c and 94d in the illustrated embodiment. The angles between the segments turn the segments so that they partially enclose a space 100 on what may be considered an "internal" side of bracket 92.

Bracket 92 includes an elongated extension 102 that extends from end 96 substantially perpendicular to segment 94a and into or further bounding space 100. The exterior of extension 102 is square or rectilinear at least in part at the junction with segment 94a in the illustrated embodiment for ease of manufacture and for maintenance of rigidity of bracket 92, and may be cylindrical or remain rectilinear as one moves along it away from segment 94a. A medial portion 104 of the exterior of extension 102 is conical or linearly tapered toward a distal cylindrical end portion 106. End portion 106 is of an outer diameter slightly smaller than the end of the taper of medial portion 104, so that a ledge 108 is formed between them. End portion 106 has two extending fingers 110 that have a part-cylindrical exterior conforming with the rest of cylindrical portion 106.

An internal lumen 112 extends all the way from an exit 114 through end portion 106 through the junction between extension 102 and segment 94a to an exit 116 in segment 94a in the illustrated embodiment. Lumen 112 is of a substantially constant internal diameter in end portion 106, medial portion 104 and into or through the junction between extension 102 and segment 94a. In the junction or in segment 94a, lumen 112 widens into a chamber 118. A groove 120 cut in chamber 118 has a wider internal diameter than that of chamber 118, and divides chamber 118 into upper and lower portions. The upper portion is internally threaded with a thread 122 having an internal (crest) diameter that is approximately the same as or slightly larger than the internal diameter of the remainder of chamber 118. The lower portion is smooth, e.g. non threaded. Lumen 112 is straight, having a central longitudinal axis that is along one line throughout.

Assembly 90 further includes an attachment bolt 124 placed inside lumen 112. Bolt 124 has a shaft 126 having an externally threaded tip 128 and a head portion 130 with an internal print 132. The outer diameter of shaft 126 (including the external or crest diameter of threaded tip 128) is slightly smaller than the internal diameter of lumen 112 below chamber 118, so that shaft 126 is able to turn easily within lumen 112 but has little if any side-to-side play. Head 130 likewise has a width that is slightly smaller than the internal diameter of chamber 118 in this embodiment, again so that it can turn easily without significant play. Minimizing side-to-side play between bolt 124 and lumen 112 can assist in maintaining firm guidance by assembly 90. Bolt 124 can be easily inserted into lumen 112 from the top (through segment 94a), with shaft 126 and head 130 sliding through lumen 112 (including thread 122) until head 130 rests against the bottom of chamber 118. A C-shaped sealing spring (not shown) may be placed within groove 120 which extends at least slightly into chamber 118 to prevent bolt 124 from falling out of lumen 112 through exit 116 in segment 94a.

Segment 94a includes a second lumen 134 in the illustrated embodiment which is parallel to lumen 112 and perpendicular to segment 94a. Lumen 134 has an internally threaded upper portion 136 and a smooth (i.e. non-threaded) lower portion 138. In a particular embodiment, the inner diameter of lower portion 138 is substantially the same as the internal (crest) diameter of the thread in upper portion 136.

Segment 94b includes a lumen 140 that is perpendicular to segment 94b and is smoothly-walled with a constant inner diameter. A groove 142 having an inner diameter greater than that of lumen 140 is provided around lumen 140 and proximate to the outer surface of segment 94b (i.e., the surface facing away from space 100).

One or more guide tubes are placed through lumen 140 for conducting further implant devices (e.g. screws or pins) toward or into nail 20 during implantation. In the illustrated embodiment, two guide tubes 144 and 146 are provided. Outer guide tube 144 has a shaft 148 and a head 150 with a lumen 152 extending through the entirety of tube 144. A groove 154 having a larger internal diameter than lumen 140 is provided in head portion 150. Shaft 148 has an external diameter approximately the same as or slightly smaller than the internal diameter of lumen 140, so that shaft 148 can pass through lumen 140. Head portion 150 has an external diameter that is larger than the internal diameter of lumen 140 to prevent tube 144 from passing entirely through segment 94b. A substantially C-shaped seal spring (not shown) can be fitted into groove 154 to hold or exert pressure around inner guide tube 146.

Inner guide tube 146 has a shaft 158 and a head 160 with a lumen 162 extending through the entirety of tube 146. Shaft 158 has an external diameter approximately the same as or slightly smaller than the internal diameter of lumen 152, so that shaft 158 can pass through lumen 152. Head portion 160 has an external diameter that is larger than the internal diameter of lumen 152 to prevent tube 146 from passing entirely through tube 144. In the illustrated embodiment, tube 146 is longer than tube 144, so that shaft 158 of tube 146 extends from the end of tube 144. Lumen 162 is sized to allow passage of a screw or other fixation member for use in the implantation and fixation of nail 20.

In the illustrated embodiment, segment 94c of bracket 92 also includes a lumen 140 just as described above with respect to lumen 140 in segment 94b, in which are placed tubes 144 and 146 as also described above. In addition, the illustrated embodiment of bracket 92 has an additional lumen 140a in segment 94c. Lumen 140a is like lumens 140, except that lumen 140a is not perpendicular to its segment 94c of bracket 92. Rather, it is angled slightly so that its central longitudinal axis intersects or crosses the axis of lumen 140 in segment 94c in or adjacent to space 100. As shown in FIG. 8, the illustrated embodiment of bracket 92 has a central plane (along which the cross section of FIG. 9 is taken) that bisects each segment 94a, 94b, 94c, and 94d. That bisecting plane includes the centers and axes of lumens 140, but the center and axis of lumen 140a is to one side of the plane. While tubes 144 and 146 through segment 94c are shown inserted through lumen 140 of segment 94c, it will be understood that tubes 144 and 146 or other devices may be instead or additionally inserted through lumen 140a.

In the illustrated embodiment, segment 94d of bracket 92 also includes a lumen 140 just as described above with respect to lumen 140 in segments 94b and 94c. While no tubes 144, 146 or other devices are shown in the drawings within lumen 140 of segment 94d, it will be understood that tubes 144, 146 or other devices could be inserted therethrough. Thus, in using assembly 90 as indicated below, one, two or three of the lumens 140 in bracket 92 can be used at the same time to hold tubes (e.g. tubes 144, 146) or other devices to assist in placing or fixing nail 20.

FIGS. 7 and 9 also show a series of holes 170 laterally through bracket 92 in each of its segments. Holes 170 are generally substantially larger in diameter than lumens 140 or 140a, and are generally perpendicular to them. Holes 170 enable the surgeon to hold and control bracket 92 more easily. For example, holes 170 allow gripping of bracket 92 by a clamp or other holding device (not shown), leaving the surgeon's or assistant's hands free for other tasks. Holes 170 also make bracket 92 lighter in weight without losing structural integrity or stability, which has been found to be an important consideration when implanting smaller pediatric bones. The weight of bracket 92 when attached to nail 20 (as described below) creates a moment or torque on parts of the pediatric bone, and reducing the weight of bracket 92 reduces that torque and its possibility of injuring the bone.

The use of the illustrated embodiments of nail 20 and assembly 90 will now be described in a particular example with respect to a femur bone, although it will be understood that similar methods and devices may be used with respect to other pediatric long bones. As noted above, nail 20 may be used to repair or support an injured, malformed or otherwise abnormal femur, and so access must be gained to the surgical site. Such access may be a relatively open procedure, or may be minimally invasive, and opens the skin and other soft tissues to access a lateral portion of the femur, inferior to the greater trochanter (e.g. below the physis of the greater trochanter). Lateral access to the medullary canal (rather than through the greater trochanter) minimizes or eliminates damage to blood vessels in and around the greater trochanter, which are vital to growth and formation of the femur in children.

In one embodiment, a trocar is inserted into the femur through the lateral access and into the body of the bone. With the soft tissue being protected by a tissue protector such as a sleeve or other over the trocar, a hollow reamer is inserted over the pin and within the sleeve. A passage is reamed along the trocar, i.e. through the lateral access and into the body of the bone to the entrance of the medullary canal, and the reamer is removed. A small tissue protector or sleeve may be inserted over the trocar and within the larger sleeve to facilitate removal of the trocar. After the trocar and smaller sleeve are withdrawn, a ball-tip guide wire is inserted into the medullary canal to a point past a fracture site or other portion needing support. The wire is adjacent the entry point of the reamer and tissue protecting sleeves.

A flexible shaft reamer is inserted over the guide wire to the bone and is used to enlarge the wire opening and/or the medullary canal, and/or to remove material from the canal in preparation for inserting nail 20. If needed, a reducer may be inserted to move bone parts together or otherwise treat the problem, and it is then removed. An exchange tube is inserted over the ball-tip guide wire to facilitate its removal and the subsequent insertion of a smooth-tip guide wire, and following the insertion of the smooth-tip wire, the exchange tube is removed. A measurement is taken along the wire to ensure that the proper length nail 20 is selected.

Prior to inserting nail 20 (or other embodiment such as nail 20') into the femur, and in some cases prior to beginning the surgical procedure, nail 20 and assembly 90 may be connected to each other. Proximal end 34 of nail 20 is brought together with the distal end 106 of extension 102 so that fingers 110 of end 106 and fingers 42 of nail 20 interengage. With nail 20 and extension 102 affirmatively connected so that fingers 42 and 110 prevent relative rotation between them, threaded end 128 of bolt 124 engages internal thread 36 of nail 20. Bolt 124 is turned by a driver (not shown) to tighten bolt 124 in nail 20, so that little or no play between bolt 124 and nail 20 exists. Thus, bolt 124 and nail 20 are firmly connected not only by their interleaved fingers 42 and 110, forming an entire cylinder in the illustrated embodiment, but also by their threaded interconnection.

An impaction rod 180 is inserted into lumen 112 by threading into threads 122. Impaction rod 180 is generally a cylinder having external threads 182 at one end that are compatible with internal thread 122 of lumen 112, and a disc-shaped flange 184 above the threads. Impaction rod 180 is threaded into lumen 112 until flange 184 tightens against the surface of segment 94a.

With nail 20 and assembly 90 so prepared, nail 20 is inserted through the reamed lateral opening in the femur and into the medullary canal. The surgeon uses a slap hammer or other appropriate tool to impact rod 180 and force nail 20 into the bone. Insertion is aided, as noted above, by end 70 of nail 20 with its tapered or radiused surface, which helps deflect and guide nail 20 into and along the medullary canal. Insertion of nail 20 continues until proximal portion 22 of nail 20 is within the bone. In particular, assembly 90 allows insertion of nail 20 so that proximal portion 22 is entirely below the surface of the greater trochanter by virtue of the configuration of extension 102. The outer diameter of the end section 106 of extension 102 is equal to the outer diameter of nail 20, and that outer diameter extends up extension 20 to ledge 108 and conical medial portion 104. Accordingly, as end 34 of nail 20 is forced below the surface of the bone, no damage to the bone or enlargement of the hole is caused, as outer diameter 106 of extension 102 simply follows nail 20 into the hole. In certain embodiments, the dimensions of nail 20 and assembly 90 are arranged so that the surgeon knows that the nail is fully and properly implanted when ledge 108 or conical surface 104 approaches the surface of the bone around the lateral opening or contacts the bone.

During the insertion of nail 20, tubes 144 and 146 may be absent from bracket 92, so as not to be jarred by the impaction of nail 20, or they may be previously placed in bracket 92. With nail 20 properly implanted, the surgeon inserts an outer tube 144 through one or more of lumens 140, depending on where he or she wishes to place a securing screw or other fixing implant. With the secure fixation of bracket 92 to nail 20, and the stability provided by bracket 92 to tube 144 via close fit of tube 144 in lumen 140 and a seal ring (not shown) around tube 144 in groove 154, lumen 152 through tube 144 steadily points to a particular channel in nail 20. For example, a tube 144 within lumen 140 of segment 94b is directed to channel 48 of nail 20, while a tube within lumen 140 of segment 94c is directed to channel 60 of nail 20, and a tube within lumen 140 of segment 94d is directed to channel 46 of nail 20. With a tube 144 inserted in the desired part of bracket 92, a trocar is passed through tube 144 to penetrate soft tissue and a drill is passed through tube 144 and the opening through soft tissue to create a hole through the bone to nail 20.

Inner tube 146 can then be inserted through tube 144. With its length being greater than that of tube 144, tube 146 reaches through the hole in the bone and to or nearly to nail 20 and the channel into which a screw is to be placed. The screw is moved through tube 146 and through the adjacent channel, and is turned to thread into bone on the other side of nail 20.

To give a particular example, a screw having a threaded shaft and a head wider than the shaft can be inserted through channel 48 of nail 20. As noted above, a tube 144 is passed through lumen 140 of segment 94b. Following insertion and withdrawal of a trocar through tube 144 to create an opening through soft tissue, and insertion and withdrawal of a drill to create an opening through bone, tube 146 is passed through tube 144 and into bone so that the end of shaft 158 of tube 146 is adjacent or within opening 52 of channel 48. The screw can be passed through tube 146 with or prior to a driving instrument so that the screw's shaft enters channel 48 through opening 52. Little or no tissue or body matter is within nail 20, and so the screw's shaft can pass through channel 48 without turning or threading. When the screw's shaft reaches opening 54 on the other side of nail 20, it engages bone, and the screw is turned to thread into the bone. As the screw's head tightens against nail 20, the turning is stopped, and tubes 144 and 146 can be removed. Similar or identical procedures are used when inserting a screw through channel 46 or channel 60. A drill separate from bracket 92 is used to drill through bone to allow screws to be inserted through holes 72 and 74 of distal portion 26 of nail 20.

It will be understood that the combination of the threaded connection of bolt 124 in thread 36 of nail 20, along with the interleaved fingers 42 and 110, provides a sturdy connection between assembly 90 and nail 20. The threaded connection provides rigidity against relative longitudinal motion and side-to-side motion between nail 20 and assembly 90, and the interengagement of fingers 42 and 110 brace against rotational motion between nail 20 and assembly 90. Fingers 42 and 110, transmit most or all of the force applied through impacting rod 180 to nail 20, so that little or no force is transmitted via the threaded connection between bolt 124 and nail 20, limiting or preventing damage to the threads. The interconnection of fingers 42 and 100 can also assist in twisting nail 20 by applying torque to assembly 20.

Once nail 20 is fixed within the bone with the necessary and/or desired screws, assembly 90 may be disconnected from nail 20. Any tubes 144 or 146 that have been used are withdrawn at least from the patient and may be withdrawn from bracket 92. Bolt 124 is turned to unscrew its distal threaded tip 128 from the thread 36 in the proximal portion 22 of nail 20. When tip 128 and thread 36 disengage, assembly 90 can be removed from contact with nail 20 and set aside. Closure of the access sites (for insertion of nail 20 and for insertion of one or more screws through nail 20) is performed.

Nail 20 as intended for a femur is constructed in two configurations, one designed for use in the left femur and one for use in the right femur. The example of nail 20 shown in the drawings is intended for the right femur. The openings 50 and 52 of channels 46 and 48 are intended to open medially (toward the middle of the patient) rather than laterally (toward the side of the patient), and opening 54 opens to the inside of the angle formed by bend 32. When so inserted, the bends and angles in nail 20 direct distal portion 26 generally laterally, while the medial portion 24 is generally parallel to the diaphysis and medullary canal, and proximal portion 22 is directed slightly laterally and posteriorly to maintain support within the femoral body, forming the "anterior bow."

While the subject matter herein has been illustrated and described in detail in the exemplary drawings and foregoing description, the same is to be considered as illustrative and not restrictive in character, it being understood that only the preferred embodiment(s) have been shown and described and that all changes and modifications that come within the spirit of the disclosure are desired to be protected. The entirety of parent application Ser. No. 12/777,369, filed May 11, 2010, is incorporated herein by reference.

What is claimed is:

1. An intramedullary nail system for use in pediatric patients, comprising:
    an intramedullary nail, said nail being a one-piece item having a proximal portion, a medial portion and a distal portion and a continuous cannula that extends through each of said portions, the cannula having an opening in a proximal end in the proximal portion of the nail and an opening in a distal end of the distal portion of the nail,
    said proximal portion having a first longitudinal axis and an end with at least one finger extending parallel to said first longitudinal axis from an end surface, said proximal portion having an internal thread along said cannula extending from said end surface toward said medial portion, said proximal portion having first and second linear channels formed through it, said first and second channels having respective first and second openings on one side of said proximal portion and a common third opening across from said first and second openings, and wherein said cannula has a substantially constant diameter between the internal thread and a first bend as viewed in a medial-lateral plane between the proximal portion and the medial portion;
    said medial portion joining said proximal portion at the first bend, the first bend forming an angle between said proximal portion and said medial portion of about 165 degrees, said medial portion having a third linear channel therethrough between fourth and fifth openings, said third channel being non-parallel to either of said first and second channels,
    said distal portion joining said medial portion at a second bend as viewed in the medial-lateral plane that forms an angle between said medial portion and said distal portion of about 175 degrees, said distal portion having fourth and fifth linear channels that are parallel to each other and a sixth linear channel between and non-parallel with said fourth and fifth channels, and wherein the medial portion has a curve in a second plane perpendicular to the medial-lateral plane, the proximal portion being linear in the medial-lateral plane, and wherein the first, second, third, fourth and fifth openings each have a respective center in the medial-lateral plane and the fourth and fifth channels have respective holes with centers in a third plane, the third plane being non-parallel to the second plane and the medial-lateral plane.

2. The system of claim 1, wherein the cannula has a longitudinal axis, and said third channel intersects said cannula substantially perpendicularly to the longitudinal axis of said cannula.

3. The system of claim 1, wherein the cannula has a longitudinal axis, and said fourth and fifth channels intersect said cannula substantially perpendicularly to the longitudinal axis of said cannula, and said distal portion having an external curved surface that extends from a tip of said distal portion at least half-way to one of said fourth and fifth channels.

4. The system of claim 3, wherein said sixth channel intersects said cannula substantially perpendicularly to the longitudinal axis of said cannula, and said sixth channel does not intersect and is substantially perpendicular to said fourth and fifth channels.

5. The system of claim 1, wherein the cannula has a constant diameter distal of the internal thread.

6. The system of claim 1, wherein the nail is adapted for insertion into the femur of a pediatric patient at a location away from the greater trochanter and diaphysis of the pediatric patient.

7. The system of claim 1, wherein the distal end portion has a curved surface viewed in longitudinal cross section, with the curved surface having a narrowest extent at a distal end of the nail through which the cannula passes, and a widest extent that is the same as a diameter of the medial and distal portions, and wherein the curved surface continuously widens from the narrowest extent to the widest extent.

8. The system of claim 7, wherein the curved surface is parabolic as viewed in longitudinal cross section.

9. An apparatus comprising:
    a one piece intramedullary nail having a proximal portion, a medial portion and a distal portion, said proximal portion having a first longitudinal axis and an end with at least one finger extending parallel to said first longitudinal axis from an end surface, said proximal portion having an internal thread extending from said end surface toward said medial portion, said proximal portion having first and second linear channels formed through it, said first and second channels having respective first and second openings on one side of said proximal portion and a common third opening across from said first and second openings;
    said medial portion joining said proximal portion at a bend in a medial-lateral plane between said proximal portion and said medial portion, said medial portion having a third linear channel therethrough between fourth and fifth openings, said third channel being non-parallel to either of said first and second channels,
    said distal portion joining said medial portion at a bend in the medial-lateral plane that forms an angle between said medial portion and said distal portion of about 175 degrees, said distal portion having at least one linear channel therethrough,
    wherein a continuous cannula extends from a first opening in a proximal end of the proximal portion and intersecting the first longitudinal axis to a second opening in a distal end of the distal portion, and wherein the cannula has a substantially constant diameter between the internal thread and the bend at which the medial portion joins the proximal portion, and wherein the medial portion has a curve in a second plane perpendicular to the medial-lateral plane, the proximal portion being linear in the medial-lateral plane, and wherein the first, second, third, fourth and fifth openings each have a respective center in the medial-lateral plane and the at least one linear channel in the distal portion have respective holes with centers in a third plane, the third plane being non-parallel to the second plane and the medial-lateral plane.

10. The apparatus of claim 9, further comprising a targeting assembly including an extension with at least one finger at a tip of said extension, said at least one finger of said extension adapted to interengage with said at least one finger of said nail.

11. The apparatus of claim 10, wherein said extension has a longitudinal axis, and wherein when said at least one finger of said extension is interengaged with said at least one finger of said nail, said extension cannot rotate around said extension axis with respect to said nail.

12. The apparatus of claim 10, wherein said extension includes a lumen therethrough, and further comprising a bolt extending through said lumen, said bolt having a threaded tip adapted to thread into said internal thread of said proximal portion of said nail.

13. The apparatus of claim 9, wherein said at least one finger includes a pair of fingers, each of said fingers having a cylindrical exterior matching an exterior of said proximal portion, and wherein said fingers define a slot between them.

14. The apparatus of claim 13, wherein said slot includes a floor adjacent said internal thread.

15. The apparatus of claim 9, wherein said medial portion has a longitudinal axis and said distal portion has a longitudinal axis, and said axis of said distal portion is bent between about 1 and 10 degrees from said axis of said medial portion when viewed in a medial-lateral plane.

16. The apparatus of claim 15, wherein said axis of said distal portion is bent about 5 degrees from said axis of said medial portion when viewed in a medial-lateral plane.

17. The apparatus of claim 9, wherein said first channel has an angle of about 45 degrees with respect to a longitudinal axis of said proximal portion.

18. The apparatus of claim 9, wherein said second channel has an angle of about 120 degrees with respect to a longitudinal axis of said proximal portion.

19. An intramedullary nail system for use in pediatric patients, comprising:

an intramedullary nail, said nail being a one-piece item having a proximal portion, a medial portion and a distal portion and a continuous cannula that extends through each of said portions, the cannula having an opening in a proximal end in the proximal portion of the nail and an opening in a distal end of the distal portion of the nail, said proximal portion having a first longitudinal axis, said proximal portion having an internal thread along said cannula extending from said end surface toward said medial portion, said proximal portion having first and second linear channels formed through it, said first and second channels having respective first and second openings on one side of said proximal portion and a common third opening across from said first and second openings, and wherein said cannula has a substantially constant diameter between the internal thread and a first bend as viewed in a medial-lateral plane between the proximal portion and the medial portion;

said medial portion joining said proximal portion at the first bend, the first bend forming an angle between said proximal portion and said medial portion of about 165 degrees, said medial portion having a third linear channel therethrough between fourth and fifth openings, said third channel being non-parallel to either of said first and second channels, said distal portion joining said medial portion at a second bend that forms an angle between said medial portion and said distal portion of about 175 degrees, said distal portion having fourth and fifth linear channels that are parallel to each other and a sixth linear channel between and non-parallel with said fourth and fifth channels, and wherein the first, second, third, fourth and fifth openings each have a respective center in an opening plane and the fourth and fifth channels have respective holes with centers in a hole plane that is non-parallel to the opening plane.

20. The system of claim 19, wherein the opening plane is coincident with or parallel to the medial-lateral plane.

* * * * *